United States Patent [19]
Efange et al.

[11] Patent Number: 5,929,087
[45] Date of Patent: Jul. 27, 1999

[54] DECAHYDROQUINOLINE-BASED ANTI-CHOLINERGIC AGENTS

[75] Inventors: S. Mbua Ngale Efange, Plymouth, Minn.; Stanley M. Parsons, Santa Barbara, Calif.

[73] Assignee: Regents of the University of Minnesota, Minneapolis, Minn.

[21] Appl. No.: 08/826,830

[22] Filed: Apr. 8, 1997

[51] Int. Cl.⁶ .................. A61K 31/47; C07D 401/04
[52] U.S. Cl. .................. 514/314; 514/278; 546/17; 546/154; 546/158; 546/164
[58] Field of Search .................. 546/164, 154, 546/158, 17; 514/314, 312

[56] References Cited

U.S. PATENT DOCUMENTS

| | | | |
|---|---|---|---|
| 5,338,852 | 8/1994 | Efange et al. | 546/188 |
| 5,358,712 | 10/1994 | Efange et al. | 424/1.65 |
| 5,457,207 | 10/1995 | Efange et al. | 546/17 |
| 5,554,752 | 9/1996 | Efange | 546/17 |

OTHER PUBLICATIONS

Binkley, P.F., et al., "Parasympathetic Withdrawal is an Integral Component of Autonomic Imbalance in Congestive Heart Failure: Demonstration in Human Subjects and Verification in a Paced Canine Model of Ventricular Failure", *JACC*, vol. 18, No. 2, 464–472, (Aug. 1991).

Brittain, R.T., et al., "The Neuromuscular Blocking Action of 2–(4–Phenylpiperidino) Cyc19ohexanol (AH 5183)", *European Journal of Pharmacology 8*, 93–99, (1969).

Buccafusco, J.J., et al., "The Effect of the Acetylcholine Transport Blocker Vesamicol on Central Cholinergic Pressor Neurons", *SYNAPSE 8*, 301–306, (1991).

Capece, M.L., et al., "Vesicular Acetylcholine Transport Inhibitor Suppresses REM Sleep", *NeuroReport*, vol. 8, No. 2, 481–484, (Jan. 20, 1997).

Erickson, J.D., et al., "Functional Identification of a Vesicular Acetylcholine Transporter and Its Expression from a "Cholinergic" Gene Locus", *The Journal of Biological Chemistry*, vol. 269, No. 35, 21929–21932, (Sep. 2, 1994).

Higgins, C.B., et al., "Parasympathetic Control of the Heart", *Pharmacological Reviews*, vol. 25, No. 1, 119–155, (1973).

Leao, R.M., et al., "Inhibition of Potassium–stimulated Acetylcholine Release From Rat Brain Cortical Slices by Two High–Affinity Analogs of Vesamicol", *Brain Research 703*, 86–92, (1995).

Marien, M.R., et al., "Suppression of In Vivo Neostriatal Acetylcholine Release by Vesamicol: Evidence for a Functional Role of Vesamicol Receptors in Brain", *Journal of Neurochemistry*, vol. 57, No. 6, 1878–1883, (1991).

Marshall, I.G., "Studies on the Blocking Action of 2–(4–Phenyl Piperidino) Cyclohexanol (AH5183)", *Br. J. Pharmac*, 38, 503–516, (1970).

Salin–Pascual, R.J., et al., "Vesamicol, an Acetylcholine Uptake Blocker in Presynaptic Vesicles, Suppresses Rapid Eye Movement (REM) Sleep in the Rat", *Psychopharmacology 121*, 485–487, (1995).

Searl, T., et al., "Acetylcholine Recycling and Release at Rat Motor Nerve Terminals Studied Using (–)-Vesamicol and Troxpyrrolium", *Journal of Physiology*, 444, 99–116, (1991).

Usdin, T.B., et al., "Molecular Biology of the Vesicular ACh Transporter", *TINS* vol. 18, No. 5, 218–224, (1995).

Varoqui, H., et al., "Cloning and Expression of the Vesamicol Binding Protein from the Marine Ray Torpedo", *FEBS Letters 342 (1994) 97–102*, 97–102, (1994).

Degrado, T.R., et al., "Evaluation of (–) [18F]Fluoroethoxybenzovesamicol as a New PET Tracer of Cholinergic Neurons of the Heart", *Nucl. Med. Biol.*, vol. 21, 189–195, (1994).

Parsons, SM et al. Progress in Brain Research, 98, pp. 175–181, 1993.

Rogers GA et al. J. Med. Chem. 32, pp. 1217–1230, 1989.

*Primary Examiner*—Evelyn Mei Huang
*Attorney, Agent, or Firm*—Schwegman, Lundberg, Woessner, and Kluth, P.A.

[57] ABSTRACT

Compounds of formula I or formula II:

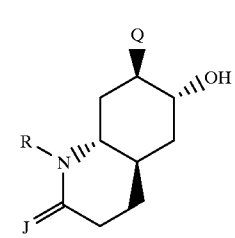

(I)

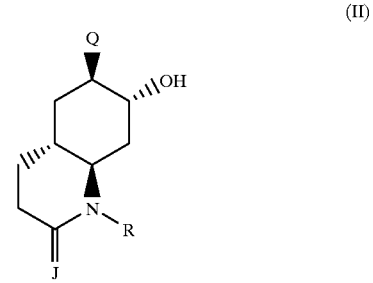

(II)

wherein R, J, and Q have any of the values defined in the specification, and their pharmaceutically acceptable salts and related radiopharmaceuticals, have anticholinergic activity, and are useful for modulating cholinergic function in mammals. Also disclosed are pharmaceutical compositions, processes for preparing compounds of formula (I) or (II) and intermediates.

15 Claims, 3 Drawing Sheets

| COMPOUND* | VAChT Ki (nM) | Sigma-1 Ki (nM) | Sigma-2 Ki (nM) | SI (Ki-σ/Ki-VAChT) |
|---|---|---|---|---|
| (−)-Vesamicol | 2.0 ± 1.0 | 26 ± 8 | 34 ± 2 | 13 |
| (±)-DPPN | 0.009 ± 0.002 | N/A | N/A | N/A |
| 1-1 | 96 ± 20 | >2,000 | >1,000 | >10 |
| 1-2 | 21 ± 5.3 | >2,000 | 25 ± 6 | 1.2 |
| 2-1 | 0.30 ± 0.06 | 110.1 ± 17.3 | 233 ± 145 | 367 |
| 2-2 | 13.10 ± 3.50 | 388 ± 178 | 41 ± 6 | 3.13 |
| (±)-3 | 0.44 ± 0.70 | 127 ± 46 | 553 ± 335 | 289 |
| 3-1 | 7.70 ± 2.0 | N/A | N/A | N/A |
| 3-2 | 0.26 ± 0.04 | N/A | N/A | N/A |
| (±)-4 | 0.99 ± 0.14 | 21.4 ± 2.6 | 127 ± 32 | 21.6 |
| (±)-5 | 0.40 ± 0.10 | 124.7 ± 2.0 | 363 ± 251 | 311.8 |
| (±)-6 | N/A | N/A | N/A | N/A |
| (±)-7 | N/A | N/A | N/A | N/A |
| (±)-8 | 5.20 ± 1.00 | 108 ± 23 | 736 ± 137 | 20.8 |
| (±)-9 | 10.00 ± 2.40 | 10.8 ± 0.9 | 345 ± 223 | 1.1 |

*Compounds 1-1,1-2, 2-1, 2-2 and 3-1, 3-2 are enantiomeric pairs which have been obtained from a Chiralcel OD column, but for which the optical rotations are currently unavailable. * Selectivity Index = Ki-σ/Ki-VAChT. N/A, Not Available.

FIG. 3

DECAHYDROQUINOLINE-BASED ANTI-CHOLINERGIC AGENTS

This invention was made with government support under NS33742 awarded by the National Institutes of Health. The government has certain rights in the invention.

BACKGROUND OF THE INVENTION

Vesamicol is a well known lipophilic analogue of the choline precursor deanol. In small to moderate doses, vesamicol induces respiratory paralysis and death in laboratory animals. Investigations of the mechanism underlying the actions of vesamicol led to the identification of a vesicular acetylcholine transporter (VAChT). VAChT is a protein complex which transports acetylcholine (ACh) from its site of synthesis in the cytosol into the synaptic vesicle. The latter serves as the primary vehicle for stimulus-induced release of acetylcholine (and other neurotransmitters) into the synapse. Vesamicol and related compounds have been shown to bind to a specific locus (the vesamicol receptor or VR) on the VAChT and thus to non-competitively inhibit the transport of ACh into the synaptic vesicle. Since the latter serves as the primary release vehicle for ACh, inhibition of synaptic vesicle loading eventually results in a cholinergic deficit at the synapse.

Consistent with this mechanism, vesamicol has no effect on pre-loaded vesicles, and vesamicol-mediated anti-cholinergic effects are frequency-dependent (reflecting the depletion of a pre-loaded vesicle pool). The identification of the VAChT provides another point for potential regulation of cholinergic function. Previously known targets include acetylcholinesterase (AChE), the sodium-dependent high affinity choline transporter (SDHAChT), choline acetyl transferase (ChAT) and muscarinic and nicotinic receptors. Moreover, the availability of vesamicol, a prototypical antagonist for the VAChT, provides an alternative method for modulating cholinergic function in the central and peripheral nervous system.

Although vesamicol is a potent inhibitor of VAChT, the compound also displays α-adrenoceptor activity. Moreover, vesamicol exhibits nanomolar affinity for sigma receptors. This lack of selectivity limits the use of vesamicol as a VAChT inhibitor. Compounds related to vesamicol are disclosed in U.S. Pat. Nos. 5,338,852, 5,358,712, and 5,457,207. Although VAChT inhibitors which are more potent and selective than vesamicol have been reported, these compounds are typically more lipophilic than vesamicol and therefore attain only limited access to the brain. Currently, there is a need for novel, potent, and selective VAChT antagonists and agonists of moderate lipophilicity, which display enhanced penetration into the central nervous system.

SUMMARY OF THE INVENTION

According to the invention there is provided a compound of the invention which is a compound of formula I or formula II:

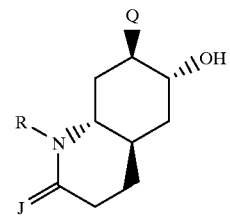

(I)

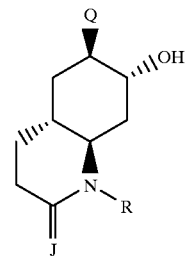

(II)

wherein

R is hydrogen, $(C_1-C_6)$alkyl, $(C_6-C_{10})$aryl, 5–10 membered heteroaryl, $(C_6-C_{10})$aryl$(C_1-C_6)$alkyl, 5–10 membered heteroaryl$(C_1-C_6)$alkyl, $(C_1-C_6)$alkanoyl, $(C_6-C_{10})$arylcarbonyl, 5–10 membered heteroarylcarbonyl, $(C_2-C_6)$alkenyl, $(C_2-C_6)$alkynyl, halo$(C_1-C_6)$alkyl, halo$(C_2-C_6)$alkenyl, or halo$(C_2-C_6)$alkynyl, wherein any aryl or heteroaryl substituent may optionally be substituted on carbon by 1, 2 or 3 Z, wherein each Z is independently halo, nitro, cyano, hydroxy, $(C_1-C_6)$alkyl, $(C_1-C_6)$alkoxy, $(C_2-C_6)$alkenyl, $(C_2-C_6)$alkynyl, $(C_1-C_6)$alkanoyl, $(C_2-C_6)$acyloxy, $S(=O)_n R_a$, $C(=O)OR_b$, $C(=O)NR_c R_d$, $NR_e R_f$, halo$(C_1-C_6)$alkyl, halo$(C_1-C_6)$alkoxy, halo$(C_2-C_6)$alkenyl, or halo$(C_2-C_6)$alkynyl;

J is two hydrogens, oxygen or sulfur;

Q is a piperidino radical of formula $I_a$, $I_b$, $I_c$ or $I_d$;

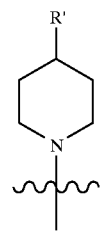

(I_a)

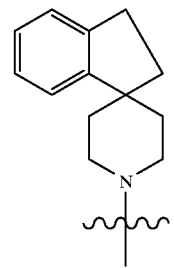

(I_b)

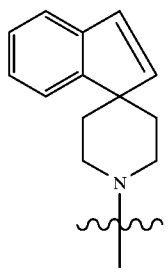

(I_c)

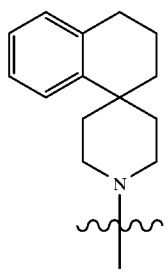

(I_d)

wherein for a radical of formula $I_a$, R' is $(C_6-C_{10})$aryl, optionally substituted by 1, 2 or 3 Z; and for a radical of formula $I_b$, $I_c$ or $I_d$, the spirocyclic group attached to the 4-position of the piperidine ring is optionally substituted by 1, 2, or 3, Z;

n is 0, 1 or 2; and $R_a$ to $R_f$ are independently hydrogen or $(C_1-C_4)$alkyl;

or a pharmaceutically acceptable salt thereof.

BRIEF DESCRIPTION OF THE FIGURES

FIG. 3 shows biological data for known compounds and for compounds of the invention.

DETAILED DESCRIPTION OF THE INVENTION

Figure 1:
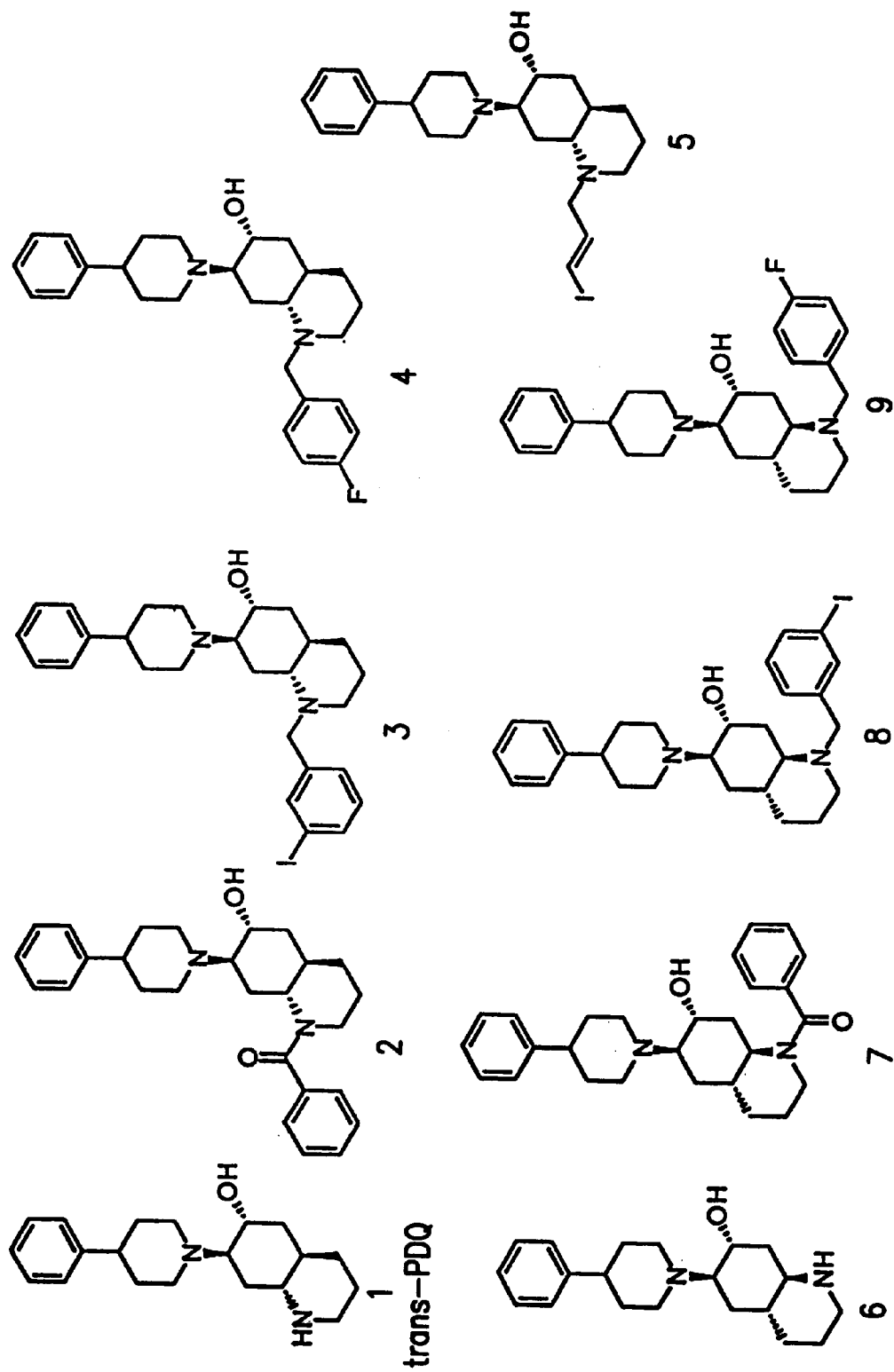
FIG. 1 shows decahydroquinilines disclosed herein.

The following definitions are used, unless otherwise described: halo is fluoro, chloro, bromo, or iodo. Alkyl, alkoxy, alkenyl, alkynyl etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) and how to determine anti-cholinergic activity using the standard tests described herein, or using other similar tests which are well known in the art.

Particular values listed below for radicals, substituents, and ranges, are for illustration only and they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexoxy; $(C_2-C_6)$alkenyl can be vinyl or allyl; $(C_2-C_6)$alkynyl can be ethynyl, 1-propynyl, or 3-propynyl; $(C_1-C_6)$alkanoyl can be acetyl, propanoyl or butanoyl; $(C_2-C_6)$acyloxy can be acetoxy, ethylcarbonyloxy or propylcarbonyloxy; halo$(C_1-C_6)$alkoxy can be fluoromethoxy, difluoromethoxy, or trifluoromethoxy; and halo$(C_2-C_6)$alkenyl can be 2-haloethyl, perfluorovinyl, perchlorovinyl, or 3-iodoallyl. Likewise, aryl can be phenyl, indenyl, or naphthyl. Heteroaryl can be furyl, imidazolyl, tetrazolyl, pyridyl, (or its N-oxide), thienyl, pyrimidinyl (or its N-oxide), indolyl, or quinolyl (or its N-oxide).

A particular group of compounds are compounds of formula I.

A particular group of compounds are compounds of formula II.

Specific compounds of the invention are compounds of formula I or II wherein Q is a radical of formula $I_a$. Other specific compounds of the invention are compounds of formula I or II wherein Q is a radical of formula $I_b$, $I_c$, or $I_d$.

Processes for preparing compounds of formulae I and II are provided as further embodiments of the invention and are illustrated by the following procedures in which the meanings of the generic radicals are as given above unless otherwise qualified. Compounds of formula I or II can generally be prepared by alkylating a piperidine corresponding to a radical of formula $I_a$, $I_b$, $I_c$, or $I_d$, with an epoxide of formula 28 under standard conditions.

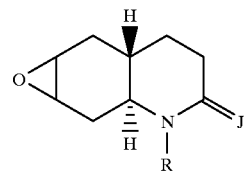

28

Solvents, bases, and reaction conditions suitable for alkylating a secondary amine with an epoxide are well known to the art. For example, the alkylation may conveniently be carried out under conditions similar to those described in Example 1.

Compounds of formula I or II, wherein R is hydrogen, can generally be prepared by hydrolysis of the corresponding amide, wherein R is an acyl group, under standard conditions. Solvents and reaction conditions suitable for hydrolyzing amides are well known to the art. For example, the hydrolysis may conveniently be carried out under conditions similar to those described in Example 5.

Compounds of formula I or II, wherein R is other than hydrogen, can be prepared by alkylating or acylating a corresponding compound of formula I or II, wherein R is hydrogen. Solvents and reaction conditions for such an alkylation or acylation are well known in the art. For example, alkylation may conveniently be carried out under conditions similar to those described in Example 6, or acylation may conveniently be carried out under conditions similar to those described in Example 1 sub-part e.

Figure 2:
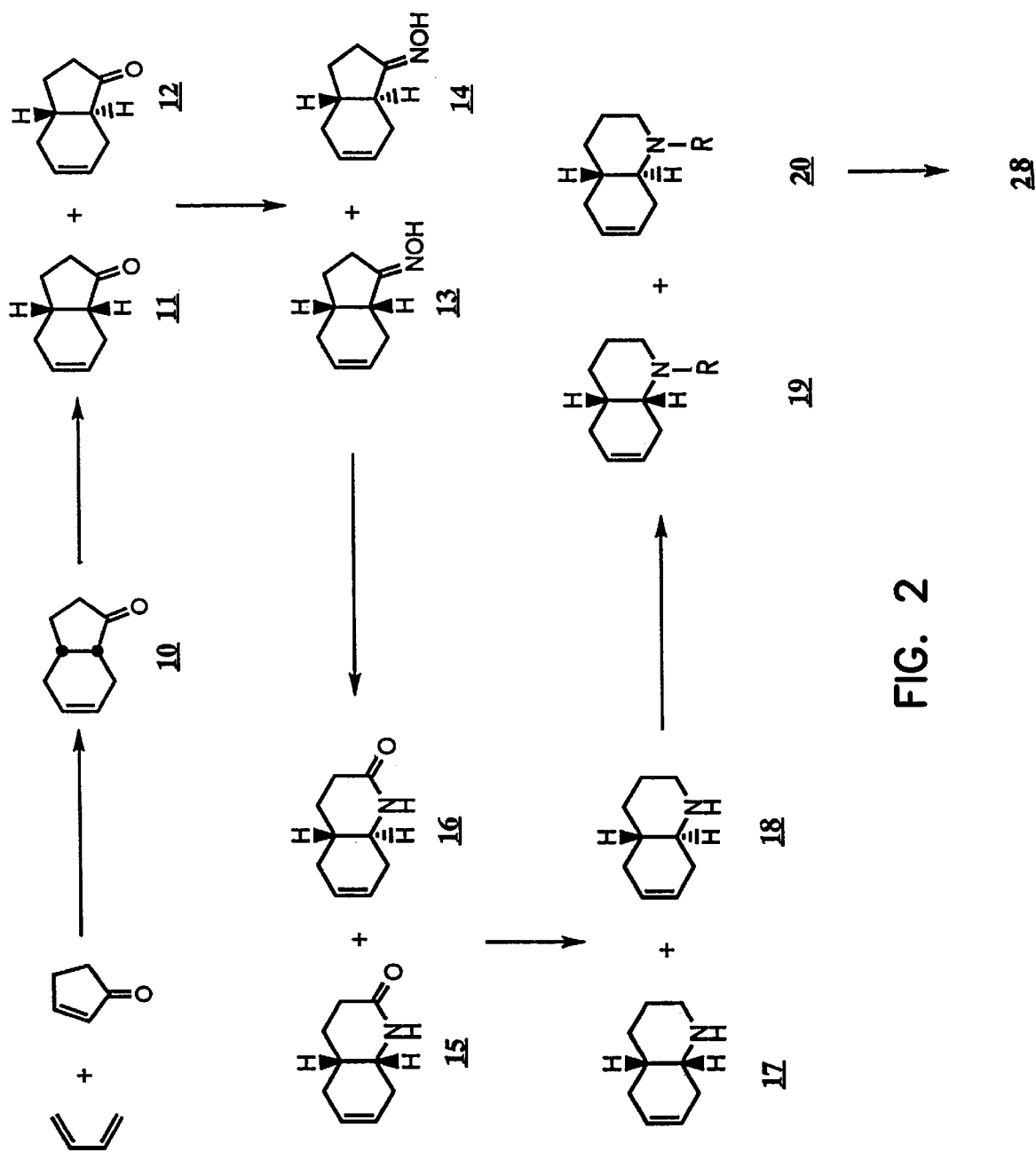
FIG. 2 shows a scheme for preparing intermediates of formulae 19 and 20.

An epoxide of formula 28 wherein J is two hydrogens can be prepared as shown in FIG. 2. Diels-Alder reaction of butadiene and 2-cyclopentenone gives a cis-tetrahydroindanone of formula 10, which can be converted to a cis/trans mixture by treatment with base. Treatment of the resulting cis/trans mixture with hydroxylamine hydrochloride and NaOAc gives a mixture of the corresponding oximes of formulae 13 and 14. Beckman rearrangement of these oximes gives octahydroquinolones of formula 15 and 16. Reduction of the quinolones yields the octahydroquinolines of formula 17 and 18. Alkylation or acylation to introduce the group R, yields compounds of formulae 19 and 20, which can be separated using standard separation techniques, for example, as described in Example 1, sub-part e. Hydrobromination of the double bond in the compound 20 followed by base catalyzed epoxide formation gives an epoxide of formula 28 wherein J is two hydrogens.

An epoxide of formula 28 wherein J is oxygen can be prepared from an intermediate of formula 16, by deprotonation with strong base in a suitable solvent, such as, for example, dimethylformamide, followed by treatment with the requsite alkyl halide or acyl halide to introduce the group R. Epoxidation of the resulting compound using known procedures, or using the procedure described in the preceding paragraph, gives an epoxide of formula 28 wherein J is oxygen.

An epoxide of formula 28 wherein J is sulfur can be prepared from an epoxide of formula 28 wherein J is oxygen using standard procedures and reagents, such as for example using the commercially available reagent [2,4-bis(4-methoxyphenyl)-1,3-dithia-2,4-diphosphetane-2,4-disulfide]. An epoxide of formula 28 wherein J is sulfur can also be prepared from an intermediate of formula 16 by introduction of the sulfur using standard procedures and reagents, followed by alkylation or acylation to introduce the group R, and epoxidation as described in the preceeding paragraph.

It is noted that many of the starting materials employed in the synthetic methods described above are commercially available or are reported in the scientific literature. The requsite piperidines are commercially available, can be prepared using methods described in U.S. Pat. No. 5,457,207, or can be prepared using methods analogous to those described in the literature.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I or II can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I or II can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I or II in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Accordingly, the invention includes a pharmaceutical composition comprising a compound of formula I and/or II as described hereinabove; or a pharmaceutically acceptable salt thereof; and a pharmaceutically acceptable diluent or carrier.

Compounds of the invention have been shown to possess anticholinergic properties. A balance between sympathetic and parasympathetic systems is required for proper cardiac function. Since a number of cardiac problems can be attributed to the loss of this balance, and since the heart receives both adrenergic and cholinergic innervation, it is clear that compounds which modulate cholinergic function can be used to restore the sympathetic-parasympathetic balance. The compounds may be useful for the treatment of cardiac arrhythmias. Accordingly, the invention includes a method for modulating cholinergic function in a mammal comprising administering to said mammal a pharmaceutically effective dose of a compound of formula I and/or II; or a pharmaceutically acceptable salt thereof. The invention also includes a method for the treatment of cardiac arrhythmia in a mammal comprising administering to said mammal a pharmaceutically effective dose of a compound of formula I and/or II; or a pharmaceutically acceptable salt thereof.

As described in U.S. Pat. No. 5,358,712, compounds of this general class may also be used as imaging agents when labeled with a radionuclide. The radionuclide (such as tritium, iodine-125, iodine-131, iodine-123, astatine-210, carbon-11, carbon-14, nitrogen-13, fluorine-18) may be attached directly to the core structure; or the radionuclide (such as Tc-99m, Re-186) may be attached to a linking group or bound by a chelating group which is then attached to the compound of formula I and/or II via a linker. Radiolabeling techniques such as these are routinely used in radiopharmaceutical chemistry. Accordingly, the invention includes a radiolabeled compound comprising a radionuclide bound to a compound of formula I or II; or a pharmaceutically acceptable salt thereof. The invention also includes a method for mapping cholinergic innervation in the brain of a mammal, comprising administering to said mammal a radiopharmaceutical composition comprising a radionuclide bound to a compound of claim 1; and a pharmaceutically acceptable diluent or carrier, and, after a suitable period of time, detecting the presence, amount, or location of said radiopharmaceutical in the brain of said mammel.

The majority of chemical agents in current use as chemical weapons target the cholinergic system. Specifically, these chemical agents inhibit the acetylcholinesterase enzymes and thus increase ACh levels in the synaptic cleft. Although a number of approaches have been used to counter or attenuate the effects of such chemical agents, none of these methods modulate the production and/or release of ACh by cholinergic neurons. Since the compounds of the invention have been shown to modulate the production and/or release of ACh by cholinergic neurons, they can be used to counter or attenuate the effects of chemical weapons. Accordingly, the invention includes a method for modulating the effects on a mammal caused by exposure to a chemical agent that inhibits the enzyme acetylcholinesterase, comprising administering to said mammal an effective amount of a compound of formula I and/or II; or a pharmaceutically acceptable salt thereof. The compound may be administered either prior to exposure or after exposure to said agent.

The anticholinergic activity of compounds of the invention can be demonstrated using standard pharmacological models such as the model described by G. A. Rogers et al. *Molecular Pharmacology*, 44, 1993, 633–641; I. G. Marshall, *British Journal of Pharmacology*, 38, 1970, 503–516; and D. Estrella et al. *British Journal of Pharmacology*, 93, 1988, 759–768. In general, compounds of the invention demonstrate significant activity in this model as shown in FIG. 3. Compounds of the invention were also evaluated for activity at the Sigma-1 and Sigma-2 receptors using the models described in S. M. N. Efange et al. *Biochemical Pharmacology*, 49,1995, 791–797.

Additionally, racemic compound 2 was tested in male Wistar rats at 11, 21, 42.5 and 85 $\mu$mol/kg. At the lowest dose, impairment of locomotor activity was observed within 4 minutes after ip injection. While some respiratory distress was also observed, the animal survived the procedure. In contrast, the higher doses induced severe respiratory distress, spasms, paralysis and death, with animals expiring within 15 minutes of drug administration (ip). These symptoms are consistent with the anticholinergic properties of the compound.

The invention will now be illustrated by the following non-limiting examples in which unless otherwise stated:

a) Synthetic intermediates were purchased from Aldrich Chemical Co. (Milwaukee, Wis.) and were used as received;

b) Tetrahydrofuran (THF) was distilled from sodium hydride immediately prior to use;

c) All other reagents and solvents were purchased as reagent grade and used without further purification;

d) Air-sensitive reactions were carried out under nitrogen;

e) Yields were not optimized;

f) Melting points were determined on a Haake-Buchler melting point apparatus and are uncorrected;

g) $^1$H NMR spectra were recorded on a 200 Mhz IBM-Brucker spectrometer or a 300 MHz GE spectrometer; NMR spectra are referenced to the deuterium lock frequency of the spectrometer, chemical shifts (in ppm) of residual solvents are observed at 7.26 (CHCl$_3$), 4.78 (CD$_3$OD);

h) Preparative chromatography was performed on Harrison Research Chromatotron using Merck 60 PF254 silica gel or a preparative HPLC system (Rainin Instrument Co.) using a 41.1 mm id Dynamax silica gel column (delivering solvent at 80 mL/minute); Chromatographic resolution of racemates and determination of enantiomeric purity was performed by HPLC using a 250 mm×10 mm id Chiralcel column (mobile phase: i-PrOH-hexane-Et$_3$N or EtOH-hexane-Et$_3$N) at a flow rate of 2.4 mL/minute;

i) Polarimetric measurements were performed with the aid of an Autopol III automatic polarimeter (Rudolph Research, Flanders, N.J., USA); and j) Analytical TLC was carried out on Analtech GHLF silica gel glass plates, and visualization was aided by UV and/or methanolic iodine.

EXAMPLES

Example 1

6,7-trans-4a,8a-trans-1-Benzoyl-7-Hydroxy-6-(4-phenylpiperidinyl)decahydroquinoline dihydrochloride (7).

The epoxide (4.27 g) from sub-part f below, 4-phenylpiperidine (3.0 g, 18.6 mmol) and Na$_2$CO$_3$ (4.0 g, 37.7 mmol) in EtOH (100 mL) was refluxed for 48 hours, cooled to room temperature and filtered to remove insoluble material. The filtrate was concentrated under reduced pressure and redissolved in chloroform (100 mL). The resulting solution was washed with water (50 mL), dried over anhydrous sodium sulfate and concentrated to a residue which was subjected to preparative HPLC (5% i-PrOH-hexanes) to provide the title compound 7 as the first compound to elute: yield, 2.1 (30%); retention time: 7.3 minutes; $^1$H NMR (CDCl$_3$) δ 150–2.52 (m, 16 H), 3.10 (m, 4 H), 3.45 (m, 2 H), 3.90(m, 1, C$\underline{H}$OH), 4.30 (m, 1, OH),7.20–7.52 (m, 10, phenyl).

The intermediate epoxide was prepared as follows.

a. Cis- and trans-3a,4,7,7a-tetrahydro-1-indanone (11 and 12).

A mixture of AlCl$_3$ (73.08 g, 548.11 mmol) and toluene (200 mL) was heated at 60° C. and a solution of 2-cyclopenenone in toluene (100 mL) was added dropwise over 30 minutes. Heating was continued for 30 additional minutes and the resulting mixture was cooled to room temperature and then to −78° C. Butadiene (100 g) was introduced over 30 minutes at that temperature without stirring. The reaction mixture was then stirred at −78° C. for 2 hours, at −10° C. for 4 hours and finally at room temperature for 18 hours. After careful dilution with ice-cold water (100 mL), and separation of the organic layer, the aqueous layer was re-extracted with ether (50 mL) and set aside. The combined organic extracts were dried over anhydrous Na$_2$SO$_4$ and concentrated to a residue. The latter was applied to a short silica gel column which was first washed with hexanes to remove hydrocarbon impurities and then with CH$_2$Cl$_2$ to elute the product. Concentration of the eluent under reduced pressure yielded 46 g (35%) of the crude cis-indanone, which was treated triethylamine (50 mL) and refluxed for 18 hours. Removal of solvent under reduced pressure afforded a quantitative yield of an equimolar cis/trans mixture of the indanone; $^1$H NMR (CDCl$_3$) δ 1.50–2.75 (m, 10, all methylene and bridgehead Hs), 5.60 (s, 2, cis-vinylic Hs), 5.70 (s, 2, trans-vinylic Hs).

b. Cis- and trans-3a,4,7,7a-tetrahydro-1-indanone oxime (13 and 14).

A 1:1 mixture of Cis- and trans-3a,4,7,7a-tetrahydro-1-indanone, 11 and 12 (69 g, 0.51 mol), hydroxylamine hydrochloride (105.69 g, 1.52 mol) and NaOAc (126.04 g, 0.933 mol) was stirred in MeOH (500 mL) for 18 hours, filtered to remove insoluble material and concentrated to a residue. The latter was partitioned between water (150 mL) and CHCl$_3$ (100 mL). Separation of the layers followed by drying of the organic extract over anhydrous sodium sulfate and eventual concentration of the resulting extract yielded 43 g (56%) of the oximes; $^1$H NMR (CDCl$_3$) δ 1.50–2.75 (m, 10 H), 5.60 (s, 2, cis-vinylic Hs), 5.70 (s, 2, trans-vinylic Hs).

c. Cis and trans-2-Oxo-1,2,3,4,4a,5,8,8a-octahydroquinoline (15 and 16).

The 1:1 mixture of oximes 13 and 14 (43 g, 0.285 mol) was dissolved in dry pyridine (500 mL) and the solution was cooled to 0° C. To this solution p-TsCl (86 g, 0.45 mol) was added portionwise over 15 minutes. The mixture was stirred at 0° C. for an additional 60 minutes, and at room temperature for 18 hours. Pyridine was evaporated under reduced pressure, and the residue was diluted with 5% aq. HCl (150 mL) and extracted with chloroform (3×100 mL). The combined organic extracts were dried over anhydrous sodium sulfate and concentrated to a residue which was passed through a short column of silica gel (eluting with 25% acetone-hexane). Concentration of the eluent provided 22 g (51%) of the crude product as a clear brown oil. This material was use without additional purification.

d. Cis and trans-1,2,3,4,4a,5,8,8a-octahydroquinoline (17 and 18).

LiAlH$_4$ (5 g, 0.132 mol) was added portionwise over 15 minutes to a stirring solution of the isomeric octahydroquinolones (22 g, 0.146 mol) in dry THF (150 mL), and the resulting mixture was refluxed under nitrogen for 18 hours. After cooling to 0° C., the reaction mixture was quenched by careful addition of water (5 mL), 15% NaOH (5 mL) and water (15 mL), consecutively. The resulting mixture was diluted with water (100 mL) and extracted with methylene chloride (2×50 mL). The combined extracts were dried over anhydrous sodium sulfate and concentrated to yield 13.4 g (67%) of a liquid containing an equimolar mixture of 17 and 18. $^1$H NMR (CDCl$_3$) δ 0.80–3.40 (m, 13 H), 5.60 (m, 2, vinyl Hs).

e. Cis and trans-1-Benzoyl-1,2,3,4,4a,5,8,8a-octahydroquinoline.

Benzoyl chloride (13 mL, 0.112 mol) was added dropwise over 5 minutes to a stirring ice-cold solution of 17 and 18 (13.4 g, 97.7 mmol). The reaction mixture was allowed to warm up to room temperature and stirred for an additional 18 hours. The resulting mixture was diluted with water (50 mL) and extracted with methylene chloride (100 mL). The organic extract was dried over anhydrous sodium sulfate and concentrated to a residue. Purification by preparative HPLC (silica gel, 2% isopropyl alcohol-hexane) yielded two major products identified as the cis and trans isomers 19 (R=benzoyl) and 20 (R=benzoyl), respectively.

Isomer 1 (compound 20, R=benzoyl): yield, 3.2 g (14%); retention time, 6.7 min. $^1$H NMR (CDCl$_3$) δ 1.26 (m, 1H), 1.58–2.18 (m, 7 H), 2.69 (br d, 1, methine H), 3.20 (m, 1H), 3.53 (m, 1H),3.91 (m, 1, methine H), 5.64 (d, 2, vinyl Hs, J=3.6 Hz), 7.37 (s, 5 H, phenyl).

Isomer 2 (compound 19, R=benzoyl): yield, (13%),; retention time, 75 min. $^1$H NMR (CDCl$_3$) δ 1.47–2.60 (m, 7 H), 3.00 (br s, 2 H), 3.55 (br s, 1H), 3.85 (br s, 1H), 4.60 (br s, 1, methine H), 5.50 (m, 2, vinyl H), 7.38 (s, 5 H, phenyl).

f. trans-1-Benzoyl-6,7-epoxy-1,2,3,4,4a,5,8,8a-octahydroquinoline.

A mixture of compound 20 (R=benzoyl) (4.0 g, 16.57 mmol) and N-bromosuccinimide (3.24 g, 18.20 mmol) was stirred in 20% aqueous THF (50 mL) for 18 hours. The reaction mixture was diluted with water (40 mL) and extracted with methylene chloride (2×50 mL). The organic extracts were combined, dried over anhydrous sodium sulfate and concentrated to afford 5.61 g (quant.) of the desired bromohydrin, which was redissolved in chloroform (100 mL) and treated with 10% NaOH (50 mL). The resulting mixture was refluxed for 2 hours and cooled to room temperature. After removal of the chloroform layer, the aqueous layer was re-extracted with chloroform (2×50 mL) and discarded. The combined organic extracts were dried over anhydrous sodium sulfate and concentrated to yield 4.27 g (quant.) of the epoxide.

Example 2

6,7-trans-4a,8a-trans-1-Benzoyl-6-hydroxy-7-(4-phenylpiperidinyl)decahydroquinoline dihydrochloride (2).

The second compound to elute from the preparative HPLC in Example 1 was isolated to give the title compound 2 0.8 g (12%); retention time, 9.1 minutes; $^1$H NMR (CDCl$_3$) δ 1.61–2.13 (m, 11 H), 2.18 (m, 3 H), 2.50 (m, 3 H),3.12 (d, 1 H),3.59 (m, 3 H), 3.82 (br d, 1, quinolyl), 3.88 (m. 1. C$\underline{H}$OH), 4.15 (m, 1, OH),7.19–7.42 (m, 10, phenyl). Anal. (C$_{27}$H$_{34}$N$_2$O$_2$. ½H$_2$O) Calcd: C, 75.83; H, 8.18; N, 6.54. Found: C, 75.44; H, 7.97; N, 6.30.

Example 3

(+)-6,7-trans-4a,8a-trans-1-Benzoyl-6-hydroxy-7-(4-phenylpiperidinyl)decahydroquinoline dihydrochloride.

Chromatographic resolution of compound 2 (0.35 g) was accomplished by HPLC using a 250 mm×10 mm id Chiralcel OD column (25% EtOH-hexane, 2.4 mL/min) to yield 120 mg of the free-base (+)-2 (retention time, 9.57 minutes), which was converted to the dihydrochloride using a procedure similar to that described in Example 6.

Example 4

(−)-6,7-trans-4a,8a-trans-1-Benzoyl-6-hydroxy-7-(4-phenylpiperidinyl)decahydroquinoline dihydrochloride.

Chromatographic resolution of compound 2 (0.35 g) was accomplished by HPLC using a 250 mm×10 mm id Chiralcel OD column (25% EtOH-hexane, 2.4 mL/min) to yield 120 mg of the free-base (−)-2 (retention time, 14.00 minutes), which was converted to the dihydrochloride using a procedure similar to that described in Example 6.

Example 5

(6,7-trans-4a,8a-trans)-6-Hydroxy-7-(4-phenylpiperidinyl)decahydroquinoline dihydrochloride (trans-PDQ (1)).

Compound 2 (0.5 g, mmol) was refluxed in 6 N HCl (25 mL) for 18 hours. The reaction mixture was cooled to room temperature and extracted with methylene chloride (2×25 mL). Concentration of the aqueous layer, followed by co-evaporation of the residue with toluene (to remove residual water) and subsequent drying under reduced pressure yielded 0.48 g (quant.) of the title compound 1 as a solid; mp 258–262° C. $^1$H NMR (CD$_3$OD) δ 6 1.70–2.15 (m, 9 H), 2.20–2.60 (m, 4 H), 2.80–3.60 (m, 9 H), 3.90 (m, 1, C$\underline{H}$OH), 7.30 (m, 5, phenyl).

Example 6

6,7-trans-4a,8a-trans-6-Hydroxy-1-(3-iodobenzyl)-7-(4-phenylpiperidinyl)decahydroquinoline dihydrochloride (IPDQ, 3).

A mixture of compound 1 (0.23 g, 0.59 mmol), 3-iodobenzyl bromide (0.26 g, 0.88 mmol) and NaHCO$_3$ (2.0 g, 23.81 mmol) in 66% aq. EtOH (15 mL) was refluxed for 18 hours. The reaction mixture was cooled to room temperature and concentrated to a residue. The latter was partitioned between methylene chloride (50 mL) and water (50 mL). The organic extract was dried over anhydrous sodium sulfate and concentrated to a residue which was passed through a short silica gel column (eluting with hexane followed by 25% acetone-hexane). Concentration of the eluent yielded the desired product as the free base. To obtain the corresponding hydrochloride, the free base was dissolved in cold methanolic HCl and the solution was concentrated under reduced pressure. The resulting hydrochloride was recrystallized from ethanol-ether to yield 0.23 g (64%) of the title compound 3; mp 249–253° C. $^1$H NMR (free base) (CDCl$_3$) δ 1.52–2.80 (m, 14 H), 2.56–2.80 (m, 3 H), 2.99–3.04 (m, 3 H), 3.50 (m, 1 H), 4.04 (m, 2 H),3.82 (br d, 1 H), 3.88 (m, 1, C$\underline{H}$OH), 4.15 (m, 1, OH), 7.04–7.71 (m, 9, phenyl). Anal. (C$_{27}$H$_{35}$IN$_2$O.2HCl.H$_2$O) Calcd: C, 52.18; H, 6.28; N, 4.50. Found: C, 52.34; H, 6.05; N, 4.48.

Example 7

(+)-6,7-trans-4a,8a-trans-6-Hydroxy-1-(3-iodobenzyl)-7-(4-phenylpiperidinyl)decahydroquinoline dihydrochloride.

Racemic 3 (0.13 g) was resolved chromatographically on a Chiralcel OD column (20% EtOH-hexane) to yield 40 mg of the title compound (+)-3 (retention time, 12.66 min), which was converted to corresponding hydrochlorides and recrystallized from EtOH-ether as described in Example 6.

Example 8

(−)-6,7-trans-4a,8a-trans-6-Hydroxy-1-(3-iodobenzyl)-7-(4-phenylpiperidinyl)decahydroquinoline dihydrochloride.

Racemic 3 (0.13 g) was resolved chromatographically on a Chiralcel OD column (20% EtOH-hexane) to yield the title compound (−)-3 (retention time, 14.85 min), which was converted to corresponding hydrochlorides and recrystallized from EtOH-ether as described in Example 6.

Example 9

6,7-trans-4a,8a-trans-1-(4-Fluorobenzyl)-6-hydroxy-7-(4-phenylpiperidinyl)-decahydroquinoline dihydrochloride (FPDQ (4)).

Using a procedure similar to that described in Example 6 except replacing the 3-iodobenzyl bromide used therein with 4-fluorobenzyl bromide, the title compound 4 was prepared; Yield, 51%; mp (hydrochloride) 145° C. 1H NMR [free base] (CDCl$_3$) δ 1.52–3.01 (m, 23 H), 4.04 (m, 2 H), 3.82 (br d, 1 H), 4.65 (s, 2, C$\underline{H}$O$\underline{H}$), 6.96–7.35 (m, 9, phenyl). Anal. (C$_{27}$H$_{35}$FN$_2$O.2HCl.½H$_2$O) Calcd: C, 64.27; H, 7.53; N, 5.55. Found: C, 64.57; H, 7.38; N, 5.45.

Example 10

6,7-trans-4a,8a-trans-6-Hydroxy-1-(3-iodoallyl)-7-(4-.phenylpiperidinyl)decahydroquinoline dihydrochloride (IAPDQ (5)).

A mixture of (±)-trans-PDQ, 1, (0.24 g, 0.62 mmol), freshly prepared trans-3-bromo-1-iodopropene (0.13 g, 0.71 mmol) and NaHCO$_3$ (2 g, mmol) was refluxed in 66% aq. EtOH (15 mL) for 18 hours. The reaction mixture was concentrated to a residue, and the latter was partitioned between methylene chloride (50 mL) and water (50 mL). The methylene chloride extract was dried over anhydrous sodium sulfate and concentrated to a residue. The latter was passed through a short silica gel column (eluting with hexane followed by 35% acetone-hexane). Concentration of the acetone-hexane eluent yielded 50 mg (17%) of the chromatographically homogeneous product. The hydrochloride was obtained by treatment with cold methanolic HCl (as described above) and the product was recrystallized from MeOH-ether to yield 40 mg of the title compound 5; mp 269–272° C. ° C.; $^1$H NMR [free base] (CDCl$_3$) δ 1.70–2.62 (m, 18 H), 2.86–3.35 (m, 5 H), 4.00 (s, 1, OH), 6.23(d, 1, C$\underline{H}$=CHi, J=15 Hz), 6.64 (m, 1, CH=C$\underline{H}$I, J=15 Hz), 7.28 (m, 5, phenyl).

Example 11

6,7-trans-4a,8a-trans-7-Hydroxy-1-(3-iodobenzyl)-6-(4-phenylpiperidinyl)decahydroquinoline dihydrochloride (8).

Using a procedure similar to that described in Example 6 except replacing the compound 1 used therein with 6,7-trans-4a,8a-trans-7-Hydroxy-6-(4-phenylpiperidinyl) decahydroquinoline dihydrochloride, the title compound 8 was prepared; yield, 54%,; mp 145° C. (dec). $^1$H NMR (DMSO-D$_6$) —δ 1.75–3.90(m, 23 H), 4.50 (m, 2, N-C$\underline{H}$-C$\underline{H}$OH), 5.80 (br s, 1, OH), 7.28 (m, 6, phenyl), 7.70 (m, 2, phenyl), 8.0 (m, 1, phenyl). Anal. (C$_{27}$H$_{35}$IN$_2$O.2HCl) Calcd: C, 53.74; H, 6.18; N, 4.64. Found: C, 47.39; H, 5.57; N, 3.90.

The intermediate compound 6,7-trans-4a,8a-trans-7-hydroxy-6-(4-phenylpiperidinyl)decahydroquinoline dihydrochloride 6 was prepared from compound 7 using a procedure similar to that described in Example 5. Compound 6 is also a compound of the invention.

Example 12

6,7-trans-4a,8a-trans-1-(4-Fluorobenzyl)-7-hydroxy-6-(4-phenylpiperidinyl)decahydroquinoline dihydrochloride (9).

Using a procedure similar to that described in Example 6 except replacing the compound 1 used therein with 6,7-trans-4a,8a-trans-7-Hydroxy-6-( 4-phenylpiperidinyl) decahydroquinoline dihydrochloride, and replacing the 3-iodobenzyl bromide used therein with 4-fluorobenzyl bromide, the title compound 9 was prepared; Yield, 54%; mp 151° C. (dec). $^1$H NMR (CDCl$_3$) [free base]δ 0.80–2.51 (m, 20 H), 2.78 (d, 1 H, J=12 Hz), 3.05 (m, 3 H), 4.05 (d, 1, J=12 Hz, N—C$\underline{H}$—CHOH), 4.16 (m, 1, C$\underline{H}$OH), 6.99 (m, 2, phenyl), 7.28 (m, 7 phenyl). Anal. (C$_{27}$H$_{35}$FN$_2$O.2HCl) Calcd. C, 65.45; H, 7.53; N, 5.65. Found: C, 60.63; H, 7.28; N, 5.12.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I or formula II:

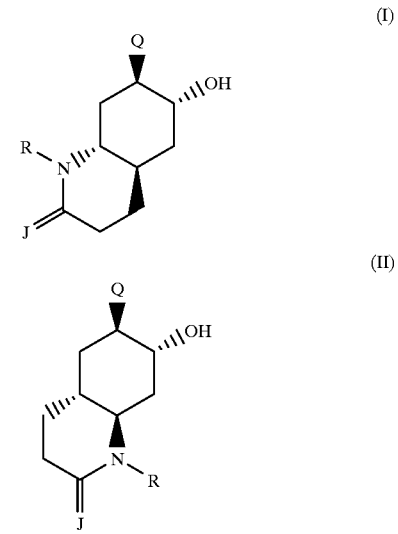

wherein

R is hydrogen, (C$_1$–C$_6$)alkyl, (C$_6$–C$_{10}$)aryl, 5–10 membered heteroaryl, (C$_6$–C$_{10}$)aryl(C$_1$–C$_6$)alkyl, 5–10 membered heteroaryl(C$_1$–C$_6$)alkyl, (C$_1$–C$_6$)alkanoyl, (C$_6$–C$_{10}$)arylcarbonyl, 5–10 membered heteroarylcarbonyl, (C$_2$–C$_6$)alkenyl, (C$_2$–C$_6$)alkynyl, halo(C$_1$–C$_6$)alkyl, halo(C$_2$–C$_6$)alkenyl, or halo(C$_2$–C$_6$) alkynyl, wherein any aryl or heteroaryl substituent may optionally be substituted on carbon by 1, 2 or 3 Z, wherein each Z is independently halo, nitro, cyano, hydroxy, $(C_1-C_6)$alkyl, $(C_1-C_6)$alkoxy, $(C_2-C_6)$alkenyl, $(C_2-C_6)$alkynyl, $(C_1-C_6)$alkanoyl, $(C_2-C_6)$acyloxy, $S(=O)_n$, $R_a$, $C(=O)OR_b$, $C(=O)NR_cR_d$, $NR_eR_f$, halo$(C_1-C_6)$alkyl, halo$(C_1-C_6)$alkoxy, halo$(C_2-C_6)$alkenyl, or halo$(C_2-C_6)$alkynyl;

J is two hydrogens, oxygen or sulfur;

Q is a piperidino radical of formula $I_a$, $I_b$, $I_c$ or $I_d$;

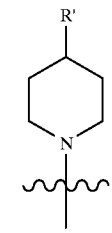

(I_a)

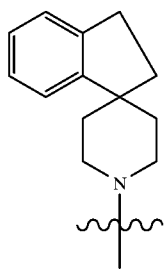

(I_b)

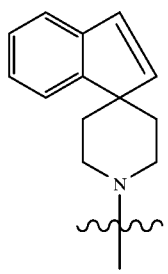

(I_c)

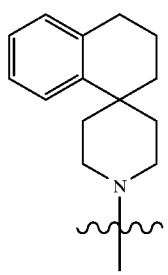

(I_d)

wherein for a radical of formula $I_a$, R' is $(C_6-C_{10})$aryl, optionally substituted by 1, 2 or 3 Z; and for a radical of formula $I_b$, $I_c$ or $I_d$, the spirocyclic group attached to the 4-position of the piperidine ring is optionally substituted by 1, 2, or 3, Z;

n is 0, 1 or 2; and $R_a$ to $R_f$ are independently hydrogen or $(C_1-C_4)$alkyl;

or a pharmaceutically acceptable salt thereof.

2. A compound of claim 1 wherein $(C_1-C_6)$alkyl is methyl, ethyl, propyl, isopropyl, butyl, iso-butyl, sec-butyl, pentyl, 3-pentyl, or hexyl; $(C_1-C_6)$alkoxy is methoxy, ethoxy, propoxy, isopropoxy, butoxy, iso-butoxy, sec-butoxy, pentoxy, 3-pentoxy, or hexoxy; $(C_2-C_6)$alkenyl is vinyl or allyl; $(C_2-C_6)$alkynyl is ethynyl, 1-propynyl, or 3-propynyl; $(C_1-C_6)$alkanoyl is acetyl, propanoyl or butanoyl; $(C_2-C_6)$acyloxy is acetoxy, ethylcarbonyloxy or propylcarbonyloxy; halo$(C_1-C_6)$alkoxy is fluoromethoxy, difluoromethoxy or trifluoromethoxy; halo$(C_2-C_6)$alkenyl is perfluorovinyl, perchlorovinyl, or 3-iodoallyl; aryl is phenyl, indenyl, or naphthyl; heteroaryl is furyl, imidazolyl, tetrazolyl, pyridyl, pyridyl-N-oxide, thienyl, pyrimidinyl, pyrimidinyl-N-oxide, indolyl, quinolyl or quinolyl-N-oxide.

3. A compound of claim 1 which is a compound of formula I.

4. A compound of claim 1 which is a compound of formula II.

5. A compound of claim 1 wherein Q is a radical of formula $I_a$.

6. A compound of claim 1 wherein Q is a radical of formula $I_b$.

7. A compound of claim 1 wherein Q is a radical of formula $I_c$.

8. A compound of claim 1 wherein Q is a radical of formula $I_d$.

9. A compound of claim 1 which is 6,7-trans-4a,8a-trans-1-benzoyl-7-hydroxy-6-(4-phenylpiperidinyl)decahydroquinoline dihydrochloride; 6,7-trans-4a,8a-trans-1-benzoyl-6-hydroxy-7-(4-phenylpiperidinyl)decahydroquinoline dihydrochloride; (+)-6,7-trans-4a,8a-trans- 1-benzoyl-6-hydroxy-7-(4-phenylpiperidinyl)decahydroquinoline dihydrochloride; (−)-6,7-trans-4a,8a-trans- 1-benzoyl-6-hydroxy-7-(4-phenylpiperidinyl)decahydroquinoline dihydrochloride; (6,7-trans-4a,8a-trans)-6-hydroxy-7-(4-phenylpiperidinyl)decahydroquinoline dihydrochloride; 6,7-trans-4a,8a-trans-6-hydroxy-1-(3-iodobenzyl)-7-(4-phenylpiperidinyl)-decahydroquinoline dihydrochloride; (+)-6,7-trans-4a,8a-trans-6-hydroxy-1-(3-iodobenzyl)-7-(4-phenylpiperidinyl)decahydroquinoline dihydrochloride; (−)-6,7-trans-4a,8a-trans-6-hydroxy- 1-(3-iodobenzyl)-7-(4-phenylpiperidinyl)decahydroquinoline dihydrochloride; 7-trans-4a,8a-trans-6-(4-fluorobenzyl)-6-Hydroxy-7-(4-phenylpiperidinyl)decahydroquinoline dihydrochloride; 7-trans-4a,8a-trans-6-(3-iodoallyl)-6-hydroxy-7-(4-phenylpiperidinyl)-decahydroquinoline dihydrochloride; 7-trans-4a,8a-trans-.1-(3-iodobenzyl)-7-hydroxy-6-(4-phenylpiperidinyl)-decahydroquinoline dihydrochloride; 7-trans-4a,8a-trans-7-hydroxy-6-(4-phenylpiperidinyl)decahydroquinoline dihydrochloride; or 6,7-trans-4a,8a-trans-1-(4-fluorobenzyl)-7-Hydroxy-6-(4-phenylpiperidinyl)decahydroquinoline dihydrochloride.

10. A pharmaceutical composition comprising a compound of claim 1 and a pharmaceutically acceptable diluent or carrier.

11. A method for inhibiting cholinergic function in a mammal by inhibiting the vesicular acetylcholine transporter comprising administering to the mammal in need thereof a dose of a compound of claim 1 effective to inhibit the vesicular acetylcholine transporter.

12. A method for treating cardiac arrhythmia in a mammal by inhibiting the vesicular acetylcholine transporter comprising administering to the mammal in need thereof a dose of a compound of claim 1 effective to inhibit the vesicular acetylcholine transporter.

13. A method for inhibiting the release of acetylcholine in a mammal exposed to a chemical agent that inhibits the enzyme acetylcholinesterase by inhibiting the vesicular acetylcholine transporter comprising administering to the mammal in need thereof a dose of a compound of claim 1 effective to inhibit the vesicular acetylcholine transporter.

14. A method as described in claim 13 wherein the the compound is administered prior to exposure to said agent.

15. A method as described in claim 13 wherein the the compound is administered after exposure to said agent.

* * * * *

UNITED STATES PATENT AND TRADEMARK OFFICE
CERTIFICATE OF CORRECTION

PATENT NO. : 5,929,087
DATED : July 27, 1999
INVENTOR(S) : S. Mbua Ngale Efange, et al.

It is certified that error appears in the above-identified patent and that said Letters Patent is hereby corrected as shown below:

In column 16, line 41, delete "7", insert --6, 7-- therefore.
In column 16, line 41, delete "6", insert --1-- therefore.
In column 16, line 43, delete "7", insert --6, 7-- therefore.
In column 16, line 43, delete "6", insert --1-- therefore.
In column 16, line 45, delete "7", insert --6, 7-- therefore.
In column 16, line 47, delete "7-trans", insert --6, 7-trans-- therefore.

Signed and Sealed this

Twenty-first Day of March, 2000

Q. TODD DICKINSON

*Attest:*

*Attesting Officer*  *Commissioner of Patents and Trademarks*